United States Patent
Kenyon (10) Patent No.: US 7,800,754 B2
(45) Date of Patent: Sep. 21, 2010

(54) OPTICAL ARRANGEMENT FOR A FLOW CYTOMETER

(75) Inventor: Oliver Kenyon, Northwood (GB)

(73) Assignee: OJK Consulting Limited, Northwood, Middlesex (GB)

(*) Notice: Subject to any disclaimer, the term of this patent is extended or adjusted under 35 U.S.C. 154(b) by 262 days.

(21) Appl. No.: 11/922,435

(22) PCT Filed: Jun. 23, 2006

(86) PCT No.: PCT/GB2006/002304

§ 371 (c)(1),
(2), (4) Date: Mar. 3, 2008

(87) PCT Pub. No.: WO2007/000574

PCT Pub. Date: Jan. 4, 2007

(65) Prior Publication Data

US 2009/0116011 A1    May 7, 2009

(51) Int. Cl.
*G01N 21/00* (2006.01)
(52) U.S. Cl. ..................... 356/337
(58) Field of Classification Search ................. 356/337
See application file for complete search history.

(56) References Cited

U.S. PATENT DOCUMENTS

| | | | |
|---|---|---|---|
| 4,441,816 A | 4/1984 | Hencken et al. | |
| 5,085,500 A | 2/1992 | Blesener | |
| 5,684,575 A | 11/1997 | Steen | |
| 6,067,157 A * | 5/2000 | Altendorf | 356/337 |
| 6,519,034 B1 | 2/2003 | Engler et al. | |
| 7,471,393 B2 * | 12/2008 | Trainer | 356/336 |
| 2004/0011974 A1 | 1/2004 | Matsuda et al. | |
| 2007/0242269 A1 * | 10/2007 | Trainer | 356/336 |
| 2008/0204716 A1 * | 8/2008 | Trainer | 356/73 |

FOREIGN PATENT DOCUMENTS

GB    2 141 553 A    12/1984

(Continued)

OTHER PUBLICATIONS

International Search Report, Corresponding to PCT/GB2006/002304, dated Oct. 6, 2006.
Written Opinion of the ISA, Corresponding to PCT/GB2006/002304, dated Oct. 6, 2006.
British Search Report, Corresponding to GB 0 513 128.9, dated Aug. 31, 2005.

(Continued)

*Primary Examiner*—Roy Punnoose
(74) *Attorney, Agent, or Firm*—Christie, Parker & Hale, LLP (57) ABSTRACT

An optical system suited to high sensitivity measurement of small particles as they travel through a point of detection in a flow cell. The system consists of components along two optical axes, preferably but not necessarily, at approximately the Brewster angle to one another. The first axis incorporates a flow cell, high numerical aperture light collection lens, spatial filtering and optical detectors. The second axis incorporates a radiation source (typically a laser or arc-lamp) and beam shaping optics. The two axes are positioned at an angle sufficient to enable collection of small angle light scatter near the edge of the collection lens and to allow collection of medium and large angle light scatter through the centre and opposite side of the collection lens. The invention enables spatial filtering in the image plane of the collection lens to exclude radiation from the dominating sources of unwanted scattering in the flow cell, and also allows the use of a high numerical aperture lens to collect radiation scattered and fluoresced by the sample particles.

3 Claims, 5 Drawing Sheets

FOREIGN PATENT DOCUMENTS

| GB | 2 272 513 A | 5/1994 |
| --- | --- | --- |
| WO | WO 96/22521 | 7/1996 |
| WO | WO 99/42809 | 8/1999 |
| WO | WO 00/57161 | 9/2000 |

OTHER PUBLICATIONS

International Preliminary Report on Patentability dated Jan. 9, 2008 for Priority International application No. PCT/GB2006/002304 indicating relevance of references cited in the Dec. 17, 2007 IDS.

* cited by examiner

OPTICAL ARRANGEMENT FOR A FLOW CYTOMETER

CROSS-REFERENCE TO RELATED APPLICATION

This application is a National Phase Patent Application of International Application Number PCT/GB2006/002304, filed on Jun. 23, 2006, which claims priority of British Patent Application Number 0 513 128.9, filed on Jun. 27, 2005.

BACKGROUND OF THE INVENTION

1. Field of the Invention

This invention relates to particle measuring and counting apparatus, as incorporated into flow cytometers. The invention is particularly well suited to the measurement of small particles such as microspheres (typically 10 nm to 10 um diameter), cells (eg blood cells or bacteria), parts of cells (eg nuclei), or viruses.

2. Description of Related Art

A flow cytometer counts, measures and discriminates particles in a liquid by their optical properties as they flow through a beam of illuminating radiation one particle at a time. The radiation source is typically a laser and the machine is normally used to count and identify particles at rates up to roughly 100000 particles per second.

The sample is normally prepared by labelling it with one or more fluorescent markers. Each fluorescent marker emits light of a characteristic wavelength range (colour) when it is excited by the laser light. The fluorescent marker may be present in the particle in a quantity roughly proportional to a substance in the particle (for example the particle's DNA content), and therefore the fluorescence signals may indicate certain features of the particle.

Flow cytometers are typically equipped with several optical detectors. Independent optical detectors may be fitted to measure light scattered at a variety of angle ranges, typically described as Small Angle Light Scatter (roughly 1 to 15 degrees, "SALS"), Medium Angle Light Scatter (roughly 15 to 60 degrees, "MALS") and Large Angle Light Scatter (typically greater than 60 degrees, "LALS"), and optical detectors to measure several different colours of fluorescence. The scatter angles are chosen to optimise the resolution between different populations of particle.

The sample liquid is hydro-dynamically focused into a narrow sample core. This may be done by a sheath fluid as it flows into the flow cell channel. Particles in the sample liquid thus pass through a point of detection in the flow cell channel one at a time and are measured individually. A light source (typically a laser) is focussed at the point of detection in the flow channel and this light is scattered by particles travelling through the flow cell. If labelled with a fluorescent marker, the particles will also emit light by fluorescence.

The scattered and fluoresced light is converted to an electrical pulse by optical detectors (typically photomultipliers), and the size and shape of these pulses is recorded by computer.

The pulse measurements are typically plotted on histogram graphs such that particles with different characteristics form distinct populations on the histograms.

It is well known that flow cytometry offers a means for counting and discriminating mammalian cells and some bacteria. However, many bacteria, archaea and viruses are too small for conventional flow cytometers to measure precisely, particularly by light scattering.

To measure differences between small particles such as bacteria, a relatively high sensitivity flow cytometer is required. It is well known that the sensitivity of a well designed flow cytometer is limited by its optical performance. The optical sensitivity may be optimised by collecting as much signal as possible from the particle, and by eliminating as much background light (noise) as possible.

BRIEF SUMMARY OF THE INVENTION

This invention presents an optical system capable of measuring small particles and resistant to optical noise from deposits on the optical surfaces of the flow cell.

The maximum signal may be achieved by collecting as much light from the point of detection as possible. This may be done by using high numerical aperture (NA) collection optics. Background light (noise) may be reduced by the use of spatial filtering and other optical filtering such as colour filters and polarisation filters.

A microscope objective lens may be used to collect light from the flow cell. For practical reasons, high NA microscope lenses have short working distances and limit the physical space around the sample and flow cell. Flow cytometers often use long working distance lenses with numerical apertures less than 1, and the laser light typically passes through the flow cell along an optical axis perpendicular to the collection optics. However, this arrangement is not practical when using a higher numerical aperture lens with a shorter working distance, as there is insufficient space around the flow cell for the incident laser beam.

Other optical designs (eg U.S. Pat. No. 5,684,575) describe optical arrangements with illumination along the same optical axis as the collection optics, but these designs typically do not allow simultaneous measurement of SALS, MALS, LALS and fluorescence signals through the same high numerical aperture collection lens, or have a more limited range of light collection angles.

According to the present invention there is provided a flow cytometer having a path through which a flow of particles is directed and an optical system having a light source arranged at a non-zero angle to the flow path other than 90° such that light scattered through a wide range of angles (including SALS, MALS and LALS sub-ranges) can be collected through the same lens.

Each sub-range can preferably be easily separated and sent to independent optical detectors. Furthermore, the means of separating each sub-range can be made operator adjustable to give the best performance for different samples, for example via software control of an electro-mechanical mirror system. Alternatively a detector array may be used (for example, as used in digital cameras) to give high resolution light scatter angular measurements.

In a second aspect the invention provides a system for measuring particles as they travel through a detection point in a flow cell, the system comprising a first set of components mounted on a first axis and comprising a flow cell and light optical collection means, and a second axis including a radiation source, wherein the axes are disposed at a non-zero angle to one another.

BRIEF DESCRIPTION OF THE DRAWINGS

Embodiments of the invention will now be described, by way of example only, with reference to the accompanying drawings, in which.

DETAILED DESCRIPTION OF THE INVENTION

Let us define:
'Region B' as being the volume of the sample stream which is illuminated by the radiation source.
'Region A' as the area of intersection of the radiation beam with the flow cell wall closest to the radiation source.
'Region C' as the area of intersection of the radiation beam with the flow cell wall furthest from the radiation source.

The present invention provides a novel and heretofore unobvious system for optically counting, measuring and differentiating particles such as bacteria, archaea, viruses and blood cells, as they travel through a flow cell. The system enables measurements of fluorescence and a wide range of light scatter angles to be taken from particles through a high numerical aperture lens. Furthermore the system achieves excellent spatial filtering of light from the measured particles through the use of a beam stop to reduce optical noise.

An optical system may provide:
collection of a wide range of scattering angles (eg from approximately 1 degree to 140 degrees) through high numerical aperture collection optics
effective spatial filtering to reduce optical noise through the use of high magnification optics and a carefully designed beam stop and thus
high measurement sensitivity (signal to noise ratio) for both light scatter and fluorescence measurements
high stability resulting from the reduced sensitivity to flow cell surface dirt/deposits
high light scatter resolution through easily adjustable scatter angle ranges (SALS, MALS, LALS)

Figure 1:
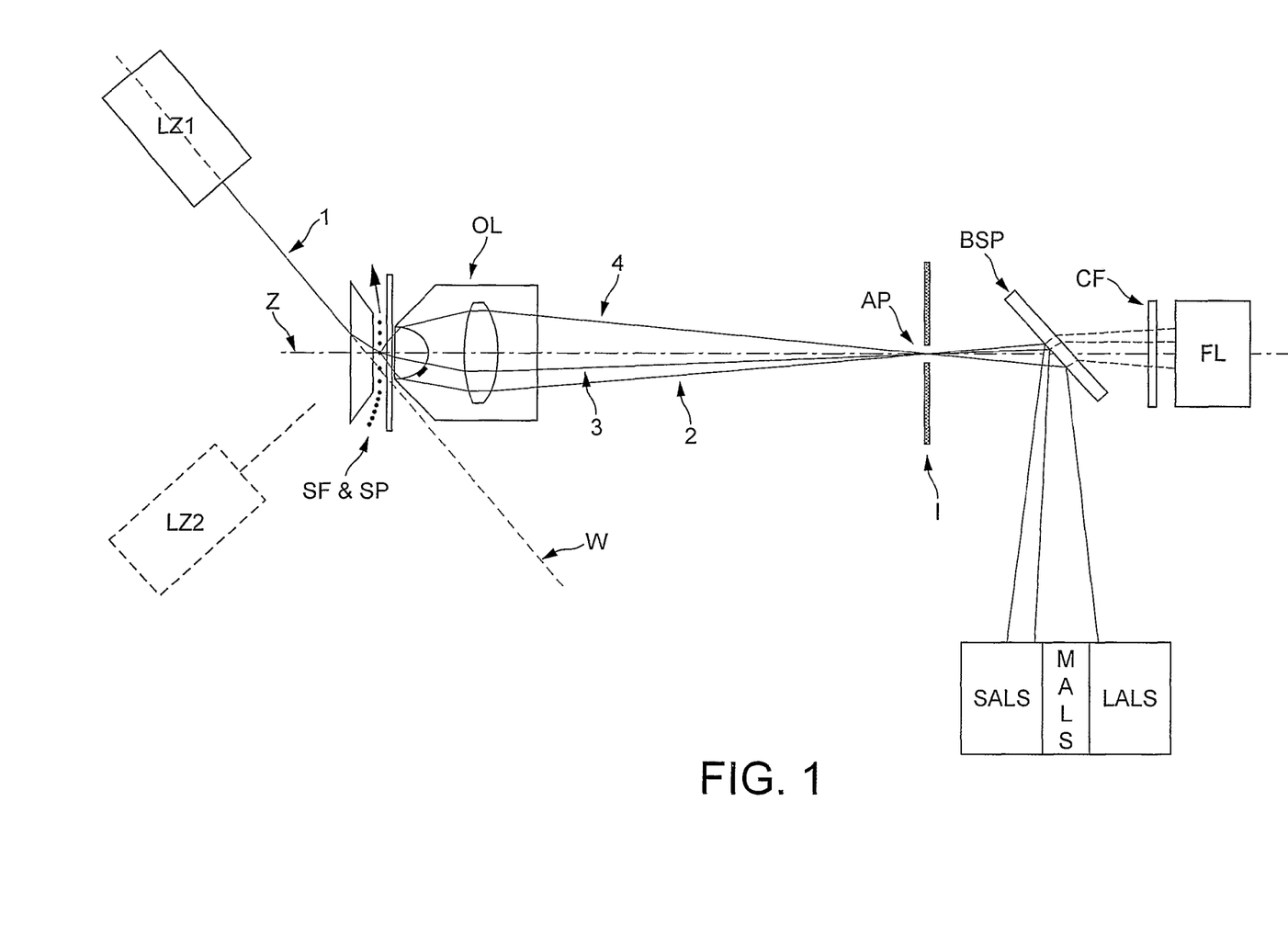
FIG. 1 is a schematic representation of an optical system.
Figure 2:
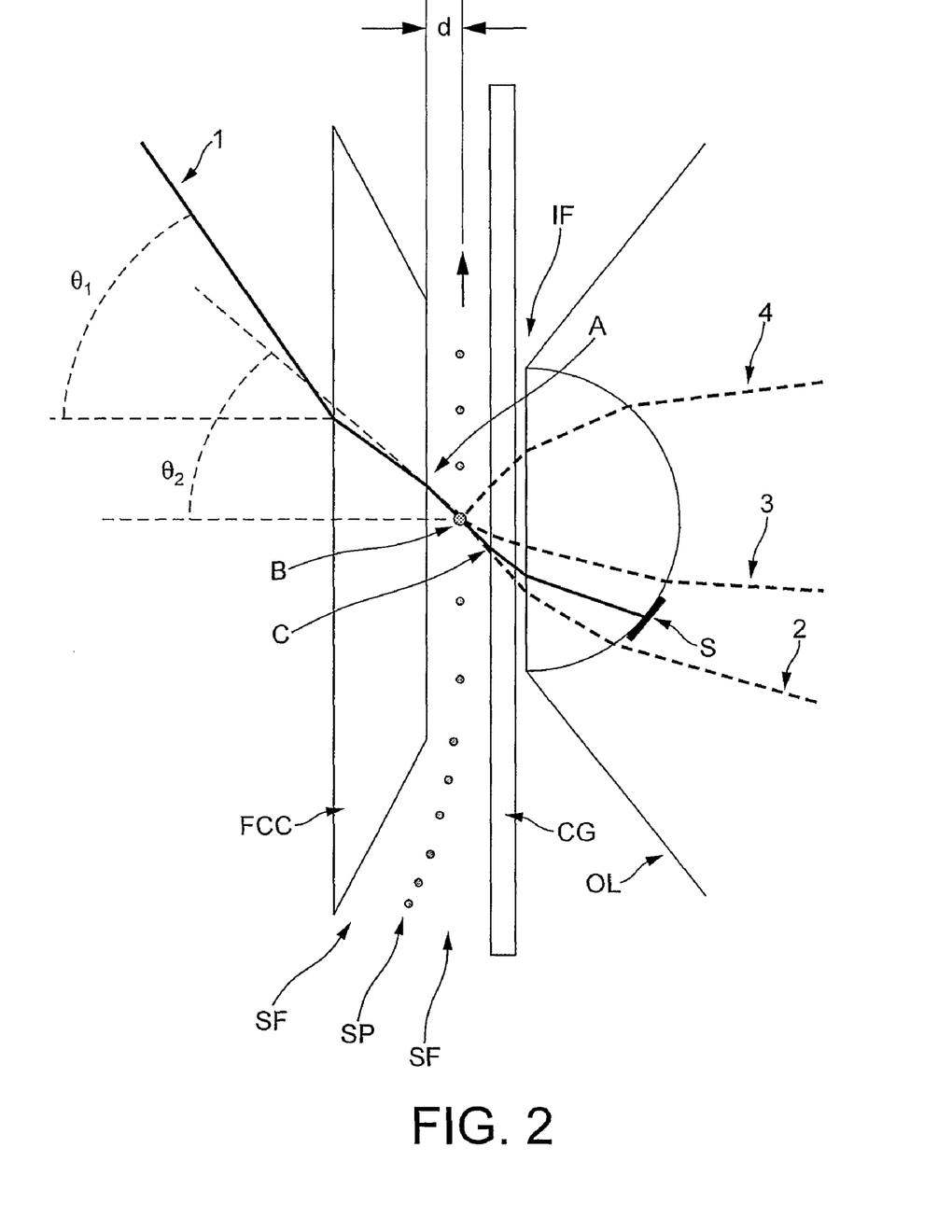
FIG. 2 is a schematic representation of light paths through a flow cell.

One such configuration, using a laser light source, is shown in FIGS. 1 and 2. Note that the light sources need not necessarily be lasers.

In the figure, a sheath fluid (SF) and sample particles (SP) are shown flowing upwards into a flow channel between a flow cell crystal (FCC) and a coverglass (CG). The sheath fluid is used to hydrodynamically focus the sample particles into a narrow stream.

A laser (LZ1) and beam shaping optics (not shown) produce a beam of radiation (1) along an optical axis (W), incident upon a flow cell crystal (FCC) at angle ($\theta_1$). The beam shaping optics may include a microscope type lens to form a well defined, bright illumination region centred on a point of detection (B) in the flow cell (FIG. 2). Suitably sized and shaped apertures may be used in the beam shaping optics to ensure only the transmission of the central part of the direct laser beam and to prevent the transmission of light which would otherwise add to background light levels (noise).

The laser beam may be shaped (for example using cylindrical optics) so as produce a focused elliptical beam which illuminates a stripe perpendicular to the sample particle stream as is well known in the art, in such a way that sample particles following slightly different paths through the flow cell are equally illuminated with intense light.

Light losses at the air to flow cell interface due to reflection may be minimised by choosing the polarisation of the illuminating laser beam such that the beam is polarized parallel to the plane containing the reflected and refracted beams (p-polarization), with the beam incident on the flow cell surface at the Brewster angle ($\theta_1 \approx 56$ degrees for a glass to air interface).

A high numerical aperture light collection optic arrangement is arranged along a second optical axis (Z).

A microscope lens (OL) is used to collect light from the flow cell channel through the coverglass (CG). An optical immersion lens fluid (IF) is typically used to fill the gap between the coverglass (CG) and microscope lens (OL) to minimise unwanted scattering and reflections at the interface and thus allow the use of high NA lenses.

The directly transmitted laser beam is prevented from travelling to a series of optical detectors (fluorescence detector (FL), SALS detector, MALS detector, LALS detector), by a beam stop (S), shaped to:
block all laser rays which have not been scattered by a sample particle (typically elliptical to match the laser beam profile at this plane in the system).
be as small as possible (without sacrificing other requirements) in order to allow some of the incident radiation scattered in Region B through small angles (for example, approximately 1 to 15 degrees), to pass on through the collection lens and through the detection aperture (AP) to a small angle light scatter detector.
be large enough to block light scattered at regions A and C which would otherwise pass through the detection aperture (AP).
ensure a similar small angle light scatter angle range is collected for particles passing through different parts of Region B in the flow cell. In particular, in order to ensure similar signal strengths for similar sample particles, it is important that approximately the same minimum angle of light scatter is transmitted to the detectors for particles travelling different paths through region B.

The beam stop is preferably positioned in the first principle plane of the collection lens.

The above requirements are generally met by an elliptical beam stop (S) and an elliptical aperture (AP). However, in some circumstances a circular aperture (AP) and beam stop (S) may suffice. To further improve the blocking of unwanted scattered laser light, a second field stop may be incorporated after the aperture (AP), in a position optically conjugate with the first beam stop (S).

Scattered rays (2, 3 and 4) pass by the beam stop and travel on to image plane (I), conjugate with the sample stream. At the image plane an aperture (AP) spatially filters light from the flow cell to exclude background scattered light. In particular, light scattered at the dominant light scattering regions A and C, where the laser beam intersects the flow cell crystal (FCC), are well spatially separated to enable effective spatial filtering by the aperture (AP) which is located in the shadow of the beam stop.

A particle at the point of detection (B) scatters light according to light scatter theory, and may also emit light by fluorescence. Radiation scattered at the point of detection through a small angle (for example rays 2 and 3) pass close to the beam stop (S). Laser radiation scattered through a large angle may also be collected by the objective lens, and will pass through the objective further away from the laser stop (4).

Fluorescence is typically emitted in all directions and the high numerical aperture lens allows a wide angle of the fluoresced light to be collected and thus maximise the amount of light reaching fluorescence detectors (FL).

This novel configuration thus provides high sensitivity light scatter and fluorescence measurements.

A dichroic beam splitter (BSP) may be located after the aperture (AP) to allow fluoresced light (of longer wavelength than the illumination light) to pass on to one or more fluorescence detectors. Additional dichroic beam splitters and detectors may be incorporated to detect several types of fluorescent molecules. The beam splitter (BSP) reflects scattered laser light towards one or more light scatter detectors (SALS, MALS and LALS).

In some embodiments, additional colour filters (CF) may be placed in front of the fluorescence detector(s) to improve signal to noise ratios. Similarly, polarisation filters may be placed in front of the light scatter detectors to measure polarisation differences between light from different particles. Colour filters may also be placed in front of the scatter detectors to block fluoresced light and to block or filter light from the spontaneous Raman effect (Raman scattering).

Lens combinations may be located in front of the optical detectors to focus light onto the sensitive parts of the detectors.

The invention allows the use of additional light (radiation) sources, typically of a different wavelength. For example, a second laser source (LZ2) may be positioned as a mirror image about the collection optical axis (Z) of the first light source (LZ1). If measuring scattered light from this second laser, a second beam stop would be required to block light not scattered in Region B, and a colour filter may be used to block light from one or other light source from reaching LALS and SALS detectors in order to ensure that only light scattered through the appropriate range of angles reaches the appropriate detector. The benefits of a second light source are well known to the art, and the second light source may be aligned to create a spatially distinct point of detection from the first light source to excite two different fluorescent dyes and/or to enable measurement of the wavelength dependence of scattering, which gives additional information about the particle (light scattering theory explains that scattering is a function of the particle characteristics and the wavelength of the light). Alternatively, radiation from more than one light source can be combined into the same beam, and then only one beam stop would be required, thus improving the collection efficiency of the collection lens. The light sources are typically lasers, diodes or arc-lamps.

Figure 3:
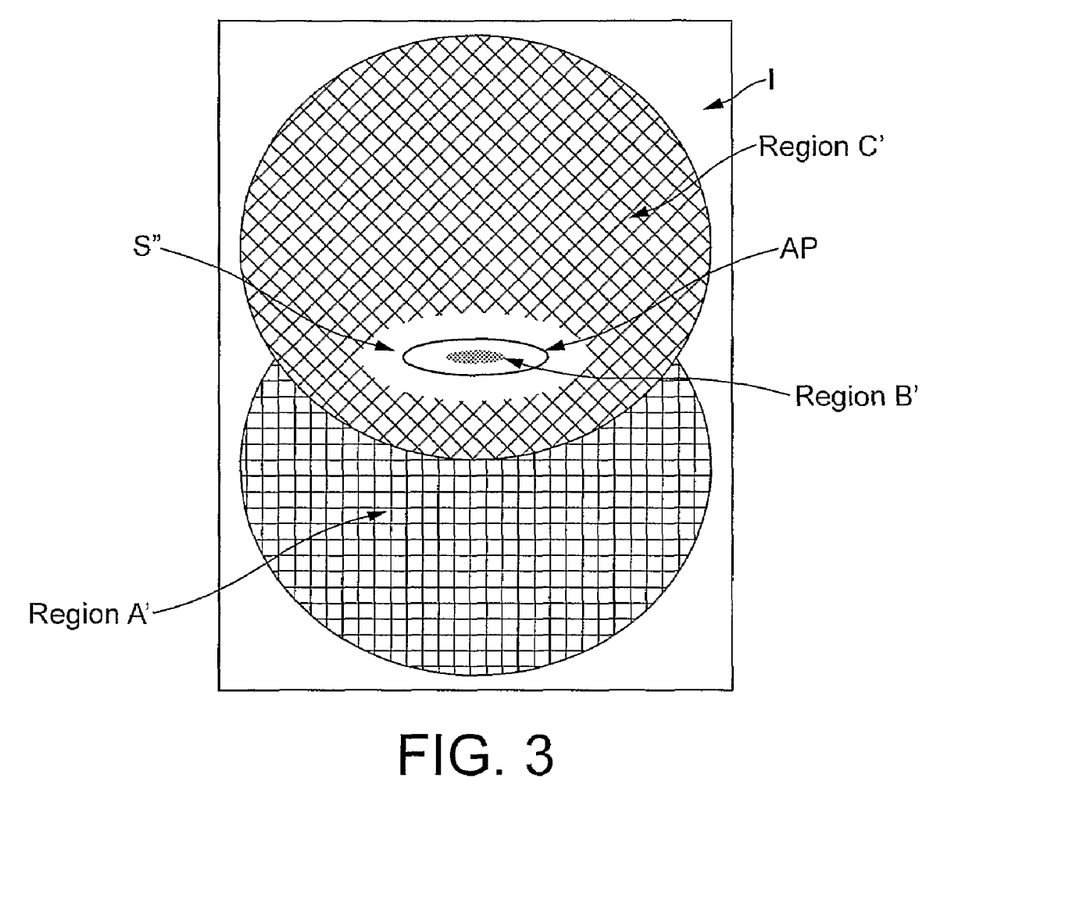
FIG. 3 shows scattered light distribution at a collection lens image plane (I) for an optical system according to one embodiment of the present invention.

FIG. 3 shows the distribution of light in the image plane (I), scattered at regions A, B and C in the flow cell (see FIG. 2). In the image plane (I), the sample stream image (B') is in focus, but the illuminated walls of the flow cell (regions A and C) are out of focus and therefore give out of focus images in Region A' and Region C'. The distribution of radiation in the image plane (I) is shown schematically for a system in which optical axes Z and W are at non-zero angle $\theta_1$ to one another. Spatial filtering of radiation B' from A' and C' gives a large reduction of background radiation which corresponds directly to a reduction of optical noise in the system. By careful choice of the size and shape of aperture (AP) to enclose region B', light scattered at critical regions A and C can be eliminated because the image (B') of region B lies within the shadow (S") cast by the beam stop (S).

The illuminating beam of radiation is typically shaped into an elliptical form using cylindrical optics and the sample particles travel in the sample core which may have a significant diameter. The size of image B' is determined by the optical magnification and the size of Region B (ie by the width of the sample core and by the illuminated length of the sample core which is typically the minor axis of the focused laser illumination).

The aperture (AP) should be small enough, and the beam stop large enough, to eliminate radiation scattered in regions A & C. The lower size limit of AP is governed by:
 1. the size of the image of the illuminated portion of the sample core (the entire image (B') of the illuminated portion of the sample core must fall inside the aperture (AP) to avoid loss of signal).
 2. Practical considerations to ensure stable and reliable operation. The smaller the aperture, the more sensitive the system will be to variations in the position of the sample core.

In this embodiment, no laser beam stop is required in the collection lens if the illuminating beam (1) is at too large an angle to axis Z for the beam to be transmitted through the collection lens (ie if the NA of the lens is too small to transmit the laser beam, then no laser beam stop is required). This configuration enables the collection of more light scattered at wide angles, and more fluoresced light, but reduces the amount of light collected at small angles as scattered light is only collected on one side of the illumination beam. This arrangement eliminates the need for a beam stop (S) to be inserted in the collection lens, and therefore avoids the loss of light which would otherwise be blocked by the beam stop.

Figure 4:
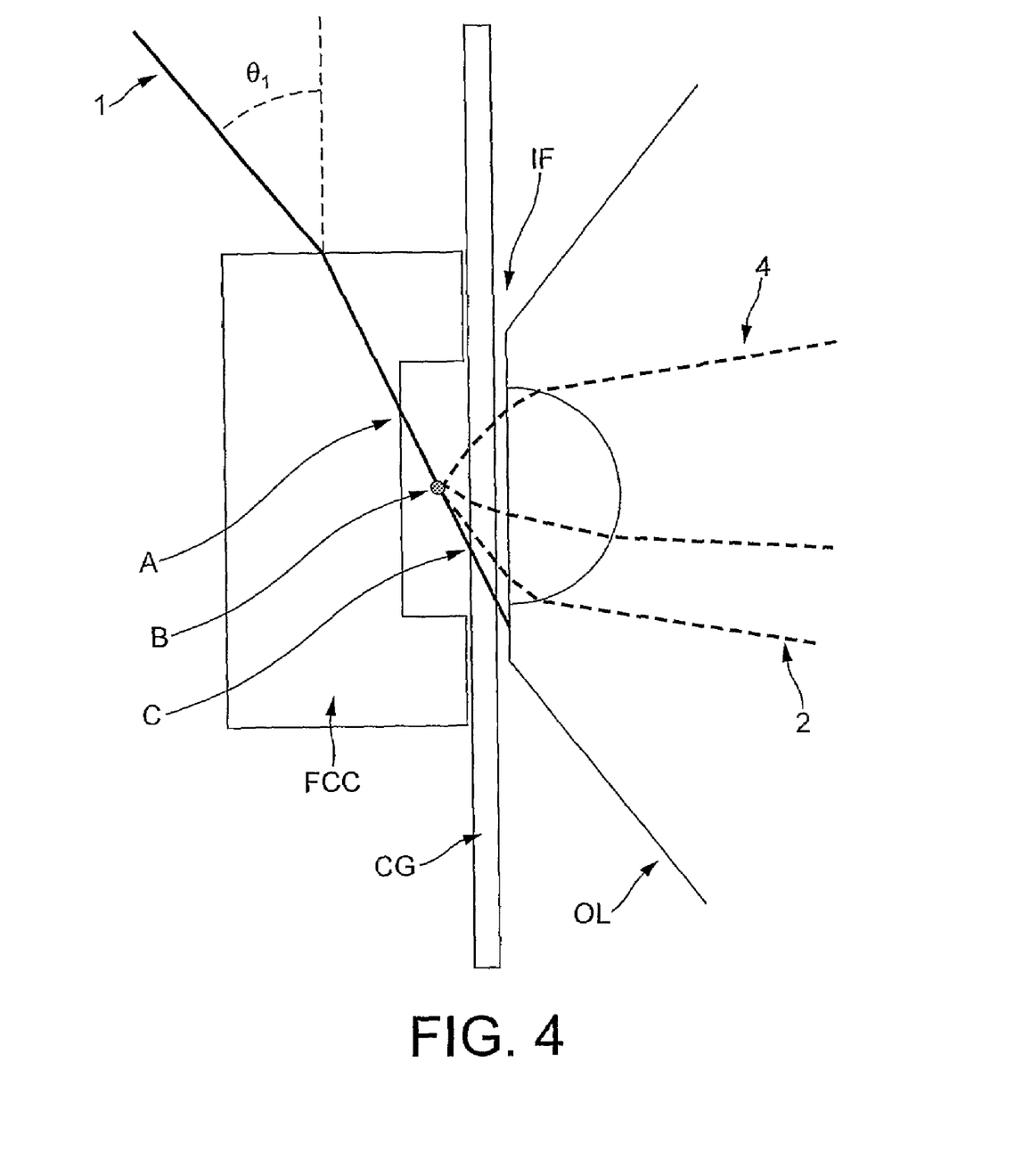
FIG. 4 shows an alternative embodiment of the invention from a direction in which the particles flow perpendicular to the page.

An alternative configuration of the invention is presented in FIG. 4. In this example, the flow path is shown by B, and so is into (or out of) the plane of the paper. The light source is arranged at a non-zero angle other than 90° to the collection optics.

In this and other embodiments, the light source may be at any non-zero angle other than 90° to the axis of the collection optics.

In addition to high sensitivity scattered light and fluorescence signals, excellent contrast between large, medium and small angle light scatter signals is possible, particularly when the laser angle ($\theta_1$) is chosen such that small angle light scatter passes close to the edge of the aperture of the collection lens to maximise the light scatter detection range. In this case large angle light scatter (LALS) and small angle light scatter (SALS) pass through opposite sides of the collection lens, and medium angle light scatter (MALS) is through the centre. The light scattered through large, medium and small angles can easily be separated by, for example, curved edged mirrors. The curvature of the edge of such mirrors, visualized in the plane perpendicular to the optical axis, should be roughly centred on the path the laser beam would tale if no laser beam stop (S) was used. In this way, light scattered by different angle ranges (SALS, MALS and LALS) can be directed to independent optical detectors. By adjusting the position of the mirrors, the operator may tune the scatter angle ranges to give the best results for different samples. Ideally the curvature of the mirrors would also be adjusted so as to maintain the position of the centre of curvature.

Improved spatial filtering could be achieved by increasing the dimensions of the flow channel to increase d (walls of the flow channel further away from the sample stream). However, a larger flow channel would have other consequences such as requiring a longer working distance collection lens, and this may not be possible to achieve without reducing the numerical aperture of the collection optics, or without significant manufacturing cost disadvantages.

Figure 5:
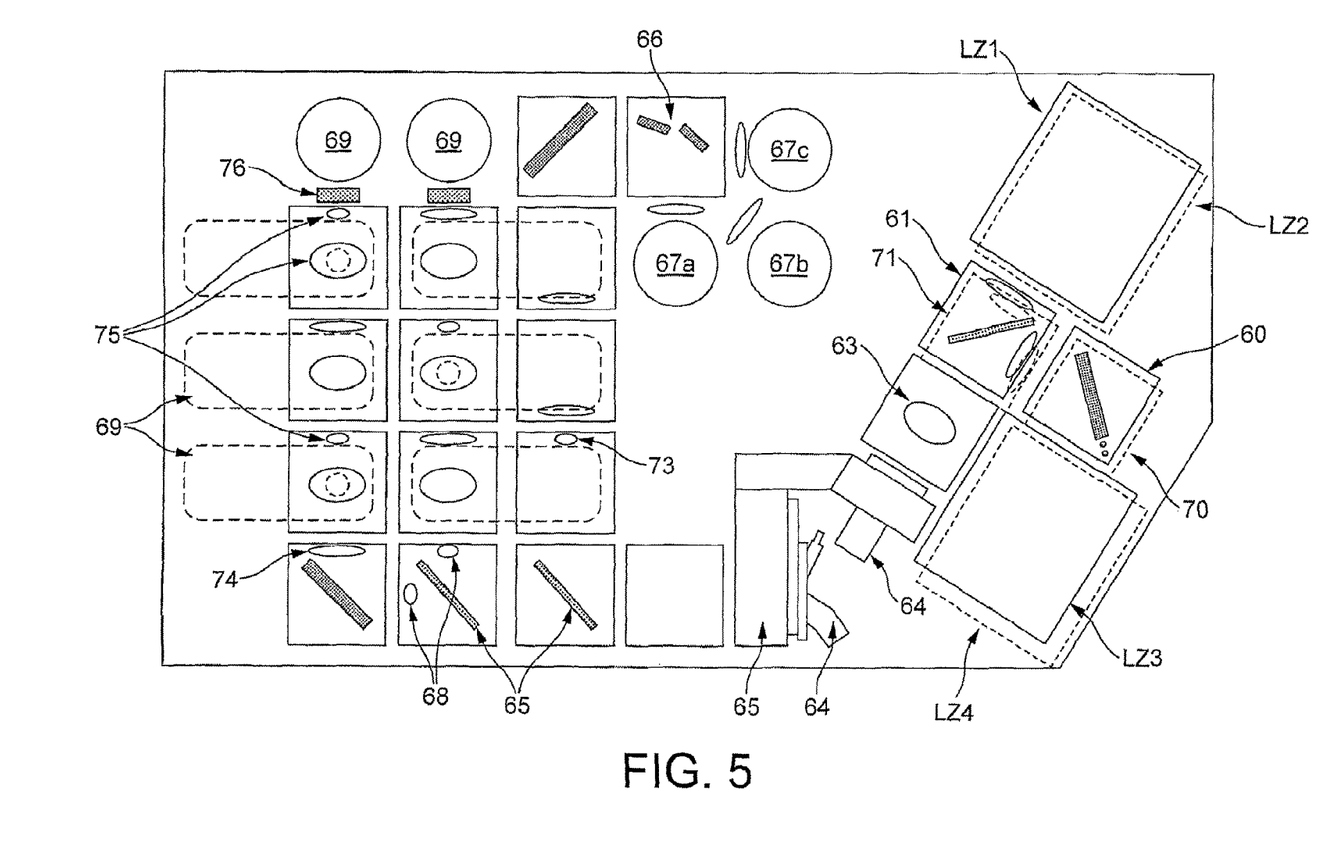
FIG. 5 shows a flow cytometer's optical system.

FIG. 5 shows an embodiment of a flow cytometer's optical system. This embodiment allows the use of up to four lasers, detection of eight different fluorescence colours and detection of three scattered light angular ranges (LALS, MALS and SALS), from sample particles in the flow cell. The fluorescence optical path has several apertures to allow discrimination between fluorescence from excitation by different (spacially resolved) lasers, and to allow for chromatic aberration. The grid arrangement allows a wide variety of optical path configurations in order to separate fluorescence and scattered light and to separate light resulting from particle illumination by different lasers. For example, the system can easily be reconfigured to use some of the fluorescence photomultipliers (PMTs) for measuring scattered light originating from a particular laser beam.

Radiation from laser LZ4 mounted on the back of the optical bench plate is reflected by mirror block 70 and then shaped by one or more cylindrical or spherical lenses and combined with the radiation beam from laser LZ2, in block 71 (also mounted on the back of the optical bench).

This combined radiation beam is directed through the optical bench plate by periscope mirror assembly 63, and combined with the radiation beams from lasers LZ1 and LZ3 by means of a dichroic beam splitter.

The radiations from LZ1 and LZ3 are directed, shaped and combined by optical blocks 60 and 61. In this way the four laser radiation beams are combined into a single beam and directed into the laser objective lens 64 which focuses the beam onto the stream of particles in the flow cell 72.

The light collection objective lens assembly 65 collects light scattered and fluoresced by particles in the flow cell 72 forms an image of the stream of particles in the fluorescence apertures 68 and light scatter aperture 73. Apertures 68 and 73 are thus in planes optically conjugate with the sample stream.

Dichroic beam splitters 65 are used to direct light of differing wavelengths towards different optical detectors.

Scattered light is reflected by a dichroic beam splitter towards the scatter aperture 73 which spatially filters light scattered by particles in the flow cell from background light (noise). Lenses after the scatter aperture create a light scatter field at mirrors 66 which is optically conjugate with the first principle plane of the collection objective lens 65. Curved edged mirrors 66 are used to direct different angle ranges of scattered light (SALS, MALS and LALS) to independent detectors 67a to c.

Additional apertures 75, optical colour filters 76, dichroic mirrors 65 and lenses 74 are used to filter and direct fluoresced light to eight optical detectors 69.

In summary, the invention offers benefits to the field of flow cytometry because its high sensitivity enables the measurement of small particles by both light scatter and fluorescence. Also, by careful choice of size and shape of the beam stop (S), the invention offers a configuration in which the light scatter background (and thus noise) is relatively insensitive to unwanted deposits/contaminants on the internal surfaces of the flow cell. Additionally, it offers a means to measure a very wide range (approximately 0 to 140 degrees) and easily adjustable sub-ranges (SALS, MALS, LALS) of scattered light, to give the best performance for different samples.

The invention therefore provides, inter alia, the following inventive features:

1. A novel optical system for measuring light scattered and fluoresced by particles in a flow cell, allowing:
    a. The use of high NA light collection optics to receive light scattered by large and small angles and fluoresced by particles flowing through a flow cell.
    b. The use of spatial filtering by an aperture, beam stop and high magnification collection lens, to eliminate scattered and fluoresced light from the surfaces of the flow cell to improve the sensitivity (signal to noise ratio).
    c. The use of a beam stop shaped to block not only the direct laser beam but also unwanted background scattered and fluoresced light from where the laser intersects flow cell surfaces.
    d. The use of Brewster's angle to maximise the laser beam transmission into the flow cell crystal from the air and to improve the polarisation of the excitation beam to improve measurements of differences between polarization preserving particles and de-polarising particles.
    e. The collection of SALS through one side of a lens and LALS through the opposite side of the lens in order to allow easy separation of light scattered through different angles, and to allow the use of high NA collection optics. The angle of the laser beam ($\theta.1$) may be chosen such that SALS rays pass near the edge of the collection lens in order to maximise the collection angle for LALS rays.
2. An optical analyzer comprising:
    a. A light source for generating a beam of light propagating along a propagation axis (W) at an angle $\theta_1$ to a second optical axis (Z). The beam passing through a point of detection (B) coincident with a sample particle stream in a flow cell (FCC).
    b. A high numerical aperture lens, spatial filtering, beam filters & dividers located along a second optical axis (Z) used to collect light scattered and fluoresced by particles travelling through the point of detection.
    c. An arrangement whereby $\theta_1$ is sufficiently large to allow collection of SALS near the edge of the collection lens and to allow collection of MALS and LALS through the centre and opposite side of the collection lens.
3. An optical system allowing measurement of light scattering from particles at a variety of ranges of scattering angles.

What is claimed is:

1. A flow cytometer having a path through which a flow of particles is directed and an optical system, the optical system having a light source arranged at angle to the axis of the optical collection means other than 90°, a collection lens allowing the simultaneous collection of small angle light scatter (SALS), medium angle light scatter (MALS) and large angle light scatter (LALS), and having an image plane; and spatial filtering means comprising an off-centre beam stop in the collection lens and an aperture in the image plane of the collection lens.

2. A flow cytometer as claimed in claim 1, wherein the particles are directed through a flow cell and the beam stop is arranged to block scatter where the light source intersects both sides of the flow cell.

3. A flow cytometer as claimed in claim 1, including a beam stop positioned in the first principal plane of a collection lens.

* * * * *

UNITED STATES PATENT AND TRADEMARK OFFICE
CERTIFICATE OF CORRECTION

Page 1 of 1

PATENT NO.        : 7,800,754 B2
APPLICATION NO.   : 11/922435
DATED             : September 21, 2010
INVENTOR(S)       : Oliver Kenyon It is certified that error appears in the above-identified patent and that said Letters Patent is hereby corrected as shown below:

On the Title Page

Insert -- (30) Foreign Application Priority Data
  June 27, 2005 (GB) 0513128.9 --

Signed and Sealed this
Thirteenth Day of September, 2011

David J. Kappos
*Director of the United States Patent and Trademark Office*